(12) United States Patent
Sommer et al.

(10) Patent No.: US 10,532,206 B2
(45) Date of Patent: Jan. 14, 2020

(54) CORONARY SINUS MEDICAL ELECTRICAL LEAD

(71) Applicant: Medtronic, Inc., Minneapolis, MN (US)

(72) Inventors: John L Sommer, Coon Rapids, MN (US); William J Clemens, Fridley, MN (US); Linda L Franke, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 608 days.

(21) Appl. No.: 14/523,240

(22) Filed: Oct. 24, 2014

(65) Prior Publication Data

US 2016/0114153 A1    Apr. 28, 2016

(51) Int. Cl.
*A61N 1/05* (2006.01)

(52) U.S. Cl.
CPC ...... *A61N 1/056* (2013.01); *A61N 2001/0585* (2013.01)

(58) Field of Classification Search
CPC .................. A61N 1/0565; A61N 2001/0585
See application file for complete search history.

(56) References Cited

U.S. PATENT DOCUMENTS

| | | | |
|---|---|---|---|
| 4,428,378 A | 1/1984 | Anderson et al. | |
| 5,052,388 A | 10/1991 | Sivula et al. | |
| 5,127,403 A | 7/1992 | Brownlee | |
| 5,387,233 A | 2/1995 | Alferness et al. | |

(Continued)

FOREIGN PATENT DOCUMENTS

| WO | 2007097859 A1 | 8/2007 |
|---|---|---|
| WO | 2009025816 A1 | 2/2009 |

OTHER PUBLICATIONS (PCT/US2015/057123) PCT Notification of Transmittal of the International Search Report and the Written Opinion of the International Searching Authority, dated Jan. 28, 2016, 12 pages.

(Continued)

*Primary Examiner* — Joseph M Dietrich

(57) ABSTRACT

The present invention may comprise an improvement to the prior art leads as disclosed above. In a preferred embodiment, the invention comprises an intravenous medical electrical lead that includes an elongated lead body. The elongated lead body comprises a length between a proximal end and a curved distal end, the lead body defining a longitudinal axis extending between the proximal end and the curved distal end. The lead body having an outer circumference and provided with a set of electrodes circumferentially spaced apart. Each electrode includes an electrically active portion and an insulated portion at an outer circumference of the electrode. The lead body is further configured to move through a coronary vein while substantially retaining its curved distal end. The lead body may freely move longitudinally within a delivery catheter that guides the lead to myocardial tissue. If the lead body rotates within the delivery catheter, the lead body is configured to rotate back into a position such that the electrically active portion of a set of electrodes faces myocardial tissue when exiting the guide catheter while the insulated portion of electrode are diametrically opposed to neural tissue such as the phrenic nerve.

16 Claims, 14 Drawing Sheets

(56) References Cited

U.S. PATENT DOCUMENTS

| | | | |
|---|---|---|---|
| 5,628,779 A | 5/1997 | Bornzin et al. |
| 5,683,445 A | 11/1997 | Swoyer |
| 5,800,465 A | 9/1998 | Thompson et al. |
| 5,925,073 A | 7/1999 | Chastain et al. |
| 5,991,668 A | 11/1999 | Leinders et al. |
| 5,999,858 A | 12/1999 | Sommer et al. |
| 6,021,354 A | 2/2000 | Warman et al. |
| 6,129,750 A | 10/2000 | Tockman et al. |
| 6,144,882 A | 11/2000 | Sommer et al. |
| 6,278,894 B1 | 8/2001 | Salo et al. |
| 6,321,123 B1 | 11/2001 | Morris et al. |
| 6,418,348 B1 | 7/2002 | Witte |
| 6,430,449 B1 | 8/2002 | Hsu et al. |
| 6,505,082 B1 | 1/2003 | Scheiner et al. |
| 6,757,970 B1 | 7/2004 | Kuzma et al. |
| 6,978,178 B2 | 12/2005 | Sommer et al. |
| 7,047,084 B2 | 5/2006 | Erickson et al. |
| 7,139,614 B2 | 11/2006 | Scheiner et al. |
| 7,313,444 B2 | 12/2007 | Pianca et al. |
| 7,383,091 B1 | 6/2008 | Chitre et al. |
| 7,532,939 B2 | 5/2009 | Sommer et al. |
| 7,601,033 B2 | 10/2009 | Ries et al. |
| 7,654,843 B2 | 2/2010 | Olson et al. |
| 7,684,863 B2 | 3/2010 | Parikh et al. |
| 7,783,365 B2 | 8/2010 | Ebert et al. |
| 7,860,580 B2 | 12/2010 | Falk et al. |
| 7,881,806 B2 | 2/2011 | Horrigan et al. |
| 7,974,705 B2 | 7/2011 | Zdeblick et al. |
| 8,005,549 B2 | 8/2011 | Boser et al. |
| 8,036,743 B2 | 10/2011 | Savage et al. |
| 8,295,943 B2 | 10/2012 | Eggen et al. |
| 8,437,866 B2 | 5/2013 | Gebauer et al. |
| 8,498,721 B2 | 7/2013 | Scheiner et al. |
| 8,755,909 B2 | 6/2014 | Sommer et al. |
| 8,825,180 B2 | 9/2014 | Bauer et al. |
| 2002/0193834 A1 | 12/2002 | Levine |
| 2003/0050681 A1 | 3/2003 | Pianca et al. |
| 2003/0105501 A1 | 6/2003 | Warman et al. |
| 2003/0163184 A1 | 8/2003 | Scheiner |
| 2003/0195603 A1 | 10/2003 | Scheiner et al. |
| 2003/0220676 A1 | 11/2003 | Helland |
| 2005/0090870 A1 | 4/2005 | Hine et al. |
| 2007/0249997 A1 | 10/2007 | Goodson, IV et al. |
| 2008/0114230 A1 | 5/2008 | Addis |
| 2009/0171381 A1 | 7/2009 | Schmitz et al. |
| 2010/0268298 A1 | 10/2010 | Moffitt et al. |
| 2011/0005069 A1 | 1/2011 | Pianca |
| 2011/0238129 A1 | 9/2011 | Moffitt et al. |
| 2012/0203316 A1 | 8/2012 | Moffitt et al. |
| 2013/0131748 A1 | 5/2013 | Stadler et al. |
| 2013/0184801 A1 | 7/2013 | Carlson et al. |

OTHER PUBLICATIONS (PCT/US2015/057251) PCT Notification of Transmittal of the International Search Report and the Written Opinion of the International Searching Authority, dated Feb. 4, 2016, 10 pages.

(PCT/US2015/057253) PCT Notification of Transmittal of the International Search Report and the Written Opinion of the International Searching Authority, dated Feb. 9, 2016, 11 pages.

(PCT/US2015/057118) PCT Notification of Transmittal of the International Search Report and the Written Opinion of the International Searching Authority, dated Mar. 14, 2016, 12 pages.

(EP Application No. 15851769.8) Communication Received from EPO Search Report, dated Jul. 2, 2018, 7 pages.

CORONARY SINUS MEDICAL ELECTRICAL LEAD

TECHNICAL FIELD

The present disclosure pertains to medical electrical leads, and, more particularly, to implantable medical electrical leads that reduce undesired neural stimulation.

BACKGROUND

Implantable medical devices, for example cardiac pacemakers and defibrillators, often include elongate medical electrical leads having one or more electrodes to sense electrical activity and deliver therapeutic stimulation. With the advent of left ventricular pacing to alleviate heart failure, leads have been advanced into the coronary veins in order to position the electrodes of the leads at left ventricular pacing sites, typically located in proximity to the base of the left ventricle. Although a variety of left ventricular pacing leads, along with methods for implanting such leads, have been developed, there is still a need for a lead including features that facilitate delivery to, and fixation at, sites in the coronary vasculature.

Numerous types of medical electrical leads can be adapted for placement in the coronary vasculature. Exemplary active fixation leads include U.S. Pat. No. 7,860,580, issued to Sommer, et al., U.S. Pat. No. 7,532,939, issued to Sommer, et al. and U.S. patent application Ser. No. 13/793,622, filed Mar. 11, 2013 by Sommer, et al., all of which are incorporated herein by reference in their entirety. Shaped leads can also be adapted for placement in the coronary vasculature. Exemplary shaped leads or catheters include U.S. Pat. No. 7,313,444, issued to Pianca et al., U.S. Pat. No. 5,387,233, issued to Alferness, et al., U.S. Pat. No. 5,925,073, issued to Chastain, et al., U.S. Pat. No. 6,430,449, issued to Hsu, et al., U.S. Pat. No. 6,129,750, issued to Tockman et al., U.S. Pat. No. 6,321,123 issued to Morris. The self-anchoring lead disclosed in Pianchi et al. includes radially spaced electrodes that are electrically active around their circumference, which can result in unwanted phrenic nerve stimulation. It is desirable to develop a coronary sinus lead that does not inadvertently cause phrenic nerve stimulation.

SUMMARY OF THE DISCLOSURE

The present disclosure may comprise an improvement to the prior art leads as disclosed above. One embodiment is directed to an intravenous medical electrical lead that includes an elongated lead body. The elongated lead body comprises a length between a proximal end and a curved distal end. The lead body defines a longitudinal axis extending between the proximal end and the curved distal end. The lead body includes a set of electrodes radially spaced apart. Each electrode includes an electrically active portion and an insulated portion at an outer circumference of the electrode. The lead body is further configured to move through a coronary vein while substantially retaining its curved distal end. The lead body may freely move longitudinally within a delivery catheter that guides the lead to myocardial tissue. If the lead body rotates within the delivery catheter, the lead body is configured to rotate back into a position such that the electrically active portion of a set of electrodes faces myocardial tissue when exiting the guide catheter while the insulated portion of the lead face neural tissue such as the phrenic nerve.

In one or more embodiments, the lead disclosed herein includes a set of electrodes in which each electrically active portion are aligned along a first longitudinal plane while a second longitudinal plane diametrically opposed to the first longitudinal plane lacks electrically active electrodes or the electrodes are insulated. The lead disclosed herein operates in a manner similar to an automobile in that the masked or insulated side is like a passenger side while the driver side is the electrically active portion of the electrode which solely directs the electrical current toward the myocardium but not by merely blasting electrical stimuli 360 degrees around each electrode. The set of electrodes of the present disclosure is similar to fuel injection vehicles that achieve more miles per gallon by minimizing the amount of current that emanates from each electrode but directing the current towards the viable tissue. Limiting the sweep of the electrical stimuli emanating from each electrode also avoids phrenic nerve stimulation.

Moreover, the medical electrical lead disclosed herein is able to achieve lower pacing thresholds to capture (i.e. evoke a response) cardiac tissue, which means less energy must be expended by the implantable medical device. Additionally, the lead results in higher pacing impedance due to use of electrodes with a decreased surface area. A higher pacing impedance decreases the current drain on the implantable medical device. Decreased current drain and energy consumption may increase the life of the implantable medical device.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments of the present disclosure will hereinafter be described in conjunction with the appended drawings, wherein like numerals denote like elements.

DETAILED DESCRIPTION

The following detailed description is exemplary in nature and is not intended to limit the scope, applicability, or configuration of the disclosure in any way. Rather, the following description provides practical illustrations for implementing exemplary embodiments of the present invention. Constructions, materials, dimensions, and manufacturing processes suitable for making embodiments of the present are known to those of skill in the field of the invention.

Figure 1:
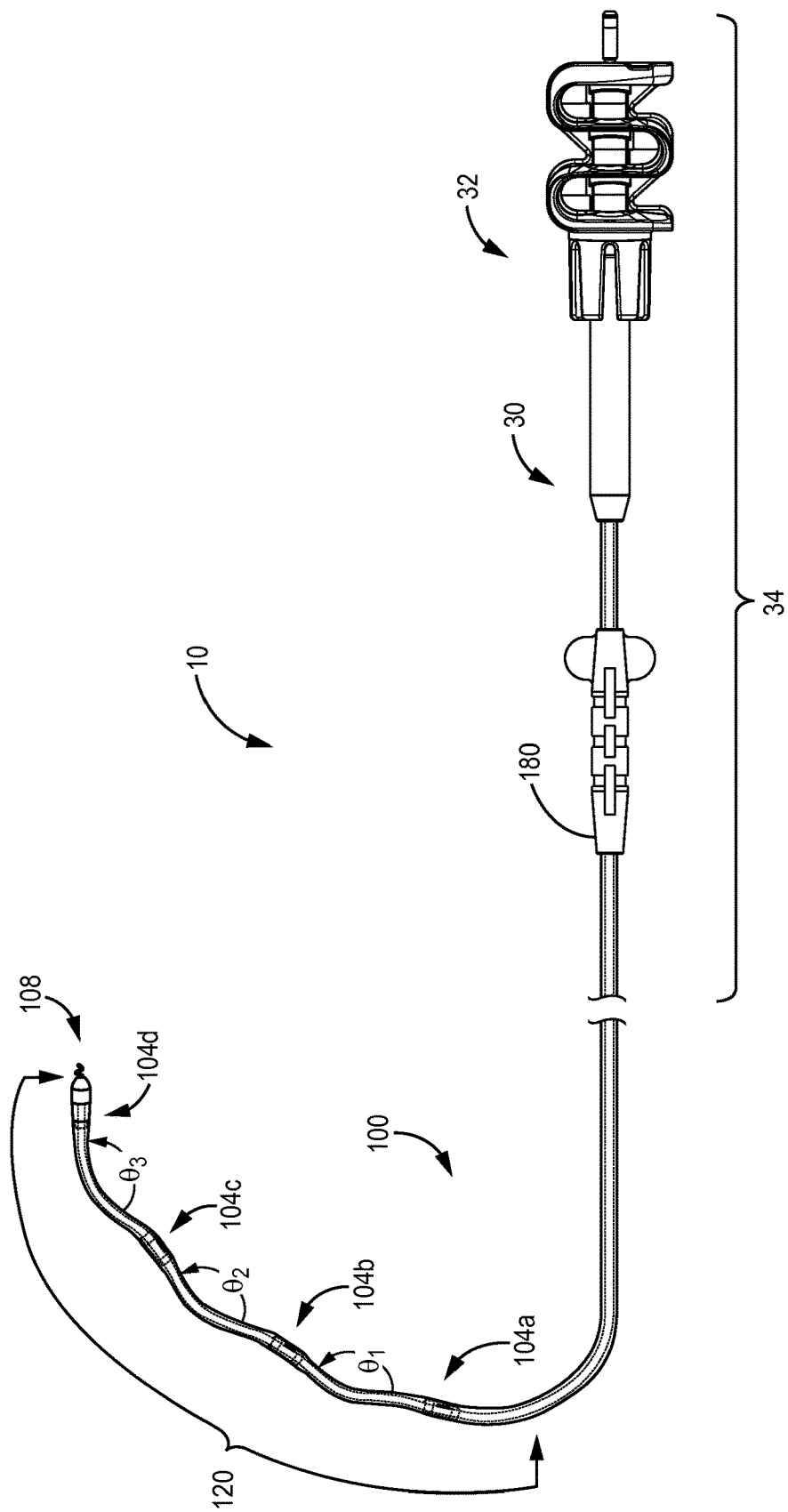
FIG. 1 is a plan view generally illustrating, a lead, according to a first embodiment.
Figure 2:
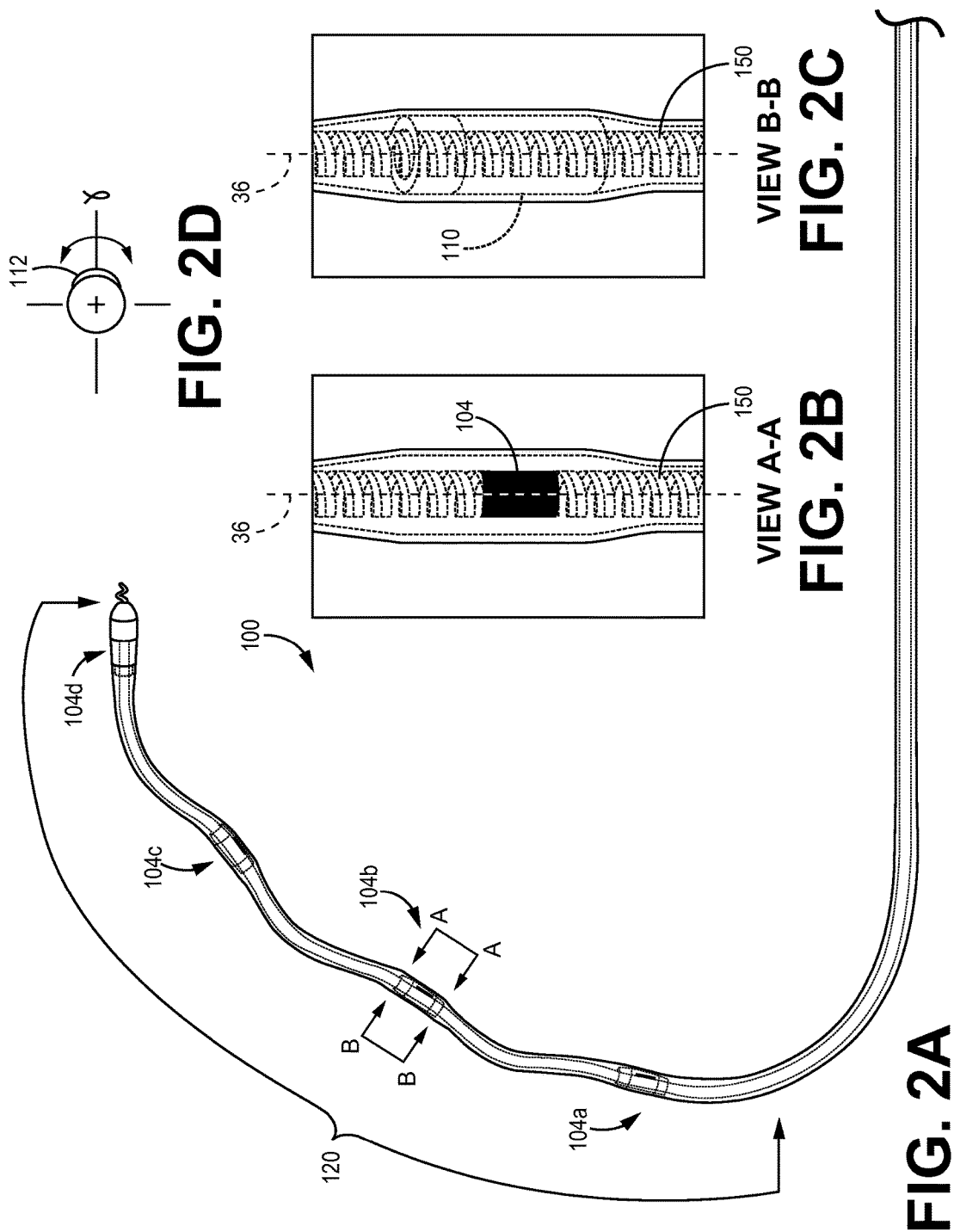
FIG. 2A is a plan view of a distal end of a lead as shown in FIG. 1, according to the embodiment in FIG. 1.
FIG. 2B is a plan view of a section of the lead in which an active portion of an electrode is shown along line A-A of FIG. 2A.
FIG. 2C is a plan view of a section of the lead in which a non-conductive portion diametrically opposed to an electrode is shown along line B-B of FIG. 2A.
FIG. 2D is a cross-sectional view of a raised electrode with an angular range shown in which electrical stimuli emanate therefrom.

FIGS. 1-2 is a plan view of an exemplary intravenous medical electrical lead 10 connected through to a guide catheter 34 such as the ATTAIN CATHETER® developed and sold by Medtronic, Inc. of Minneapolis, Minn. Lead 10 is configured to deliver electrical stimulation to tissue (e.g. ventricular cardiac pacing) and/or sense signals from the tissue. Lead 10 includes proximal end and a distal end 120 with a lead body 150 therebetween that generally defines a longitudinal axis. At the proximal end is located an in-line bipolar connector assembly 30. Distal end 120, which includes set of electrodes 104a-d (e.g. ring electrodes, directional electrodes, electrodes shown in FIG. 6 etc.), can be configured in many different ways to ensure lead 10 stays in position to deliver electrical therapy to cardiac tissue. For example, lead 10 can be fixed in a location based upon a self-anchoring shape, other passive fixation means (e.g. adhesive etc.) and/or active fixation means (e.g. tines, screw, helix etc.). The self-anchoring shaped lead is configured to wrap or hug the curved-shaped heart.

In the illustrated preferred embodiment, substantially S-shaped (or wave-shaped) distal end 120 is configured such that it may freely move longitudinally within the guide catheter but if the distal end 120 rotates, the distal end 120 will naturally reposition itself such that the electrically active portion of a set of electrodes 104a-d faces myocardial tissue during and/or after exiting the guide catheter while the insulated portion of the lead faces neural tissue (e.g. phrenic nerve). Lead 10 includes three curved areas forming angles $\theta_1$, $\theta_2$, and $\theta_3$ at distal end 120A. Each curved area is formed and maintained by creating a polymeric liner or jacket that has a durometer of about 30 D to about 50 D. Exemplary liners that can be used in conjunction with the present disclosure are shown and described with respect to U.S. Pat. No. 8,005,549 issued Aug. 23, 2011, U.S. Pat. No. 7,783,365 issued Aug. 24, 2010, and assigned to the assignee of the present invention, the disclosure of which are incorporated by reference in their entirety herein. ATTAIN PERFORMA™ Model 4298 quadripolar lead is another exemplary insulative material that can be used. In one or more embodiments, the curved polymeric liner exhibits the same or about the same stiffness as the generally linear areas of the remaining portion of the liner for the lead body 150. The curve(s) in the lead can be thermoformed using known techniques.

Figure 3:
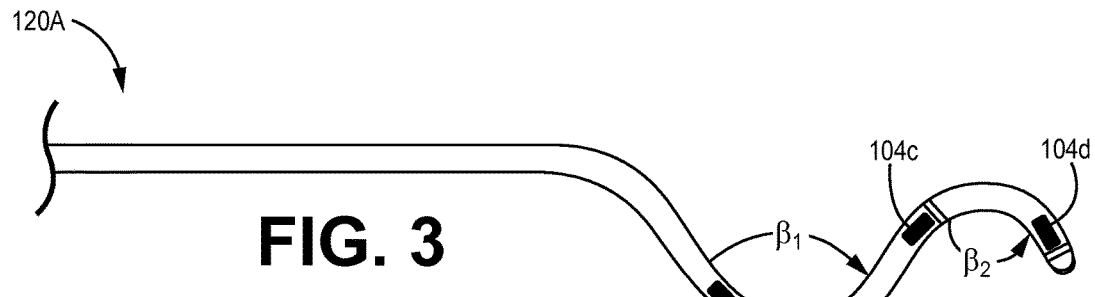
FIG. 3 is a plan view of a S-shaped distal end of a medical electrical lead, according to the embodiment in FIG. 1.

In an alternate embodiment shown in FIG. 3, the curved distal end 120B can include two curves having angles $\beta_1$ and $\beta_2$. $\beta_1$ can range from about 60 to about 80 degrees. $\beta_2$ can range from about 65 to about 85 degrees.

Figure 5:
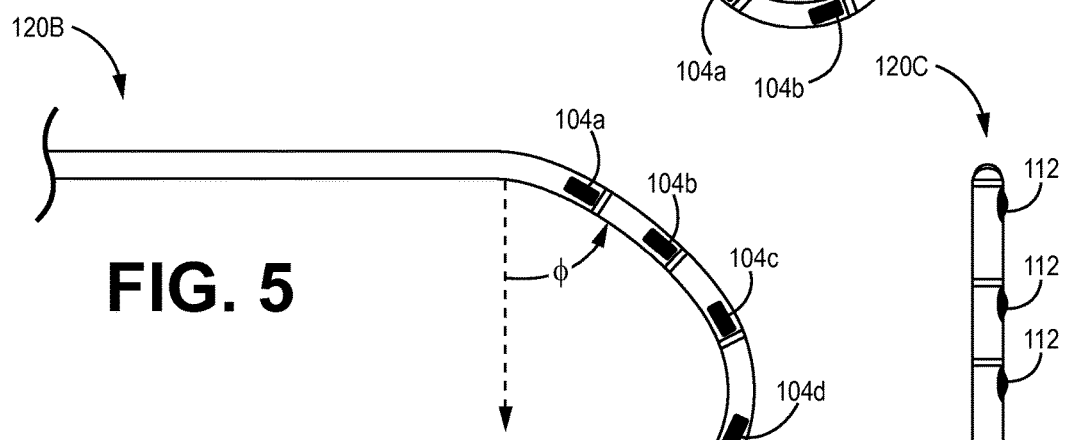
FIG. 5 is a plan view of a curved distal end of a medical electrical lead, according to a third embodiment.
Figure 4:
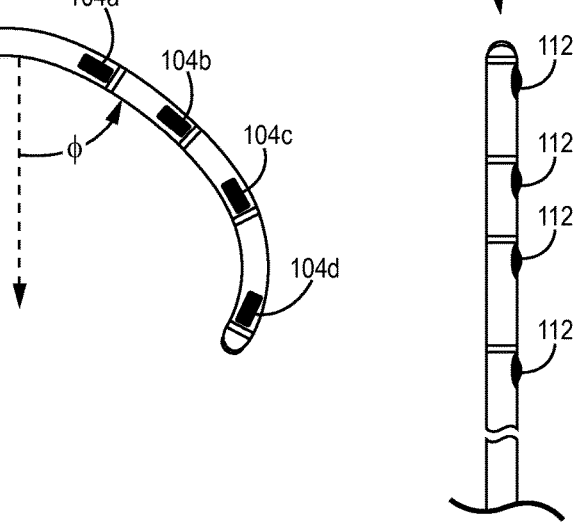
FIG. 4 is a plan view of a distal end of a substantially straight medical electrical lead with electrodes protruding away from the lead body, according to a second embodiment.

In yet another embodiment shown in FIG. 5, a lead distal end 120C can employ a single sweep curve having an angle (I) of about 90 degrees to about 180 degrees from the center line (i.e. center of the lead body) or longitudinal axis 36 of the lead body 150. In still yet another embodiment shown in FIG. 15, the distal end 120 is substantially J-shaped. J-shaped lead 400 includes an electrically active portion of electrodes on one longitudinal side of the lead 400 and an insulated portion (or lacks electrodes) on the other diametrically opposed longitudinal side of the lead 400, which is placed in proximity of neural tissue.

Figure 11:
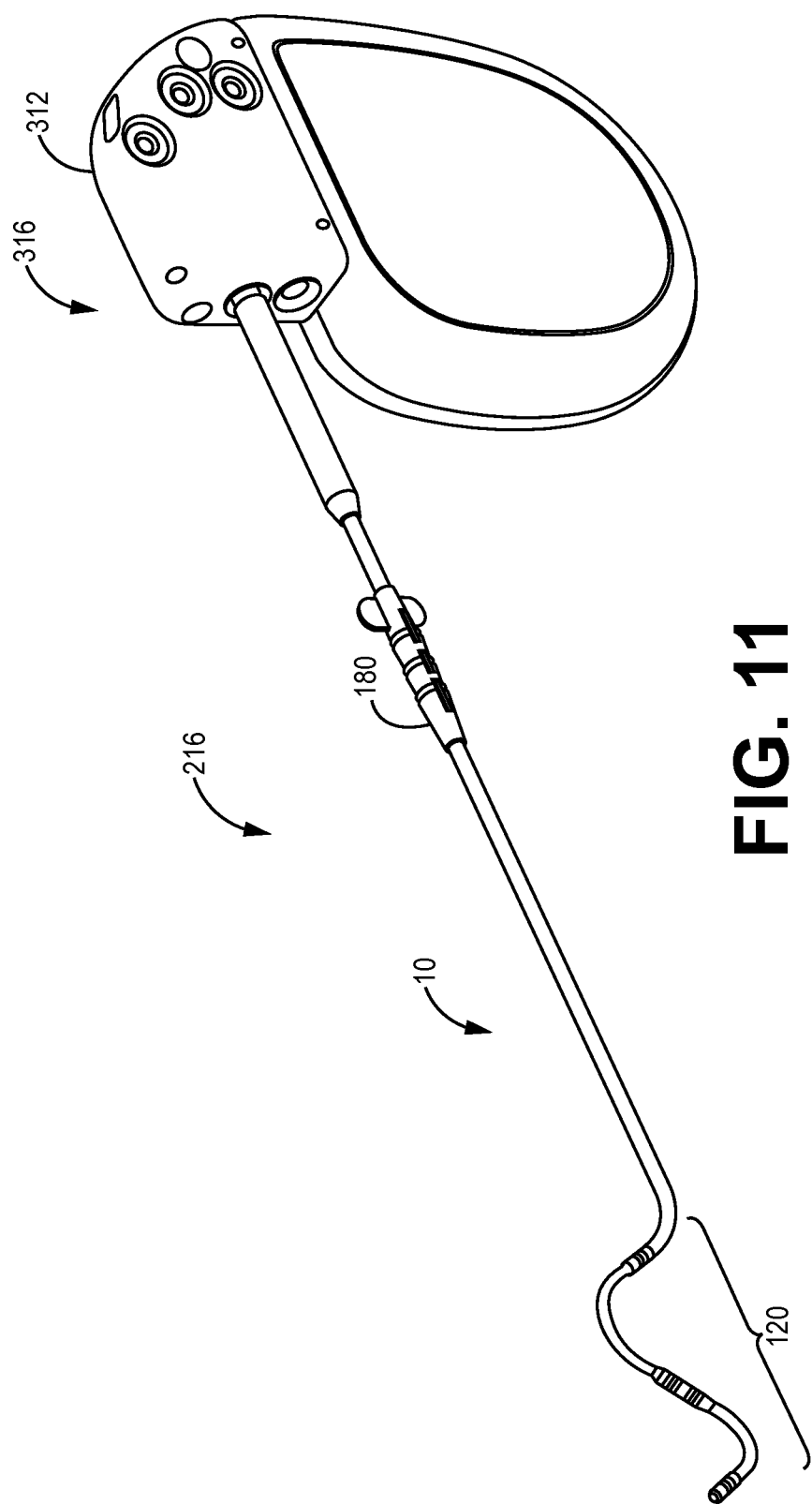
FIG. 11 is a plan diagram of an exemplary system including an exemplary implantable medical device (IMD).
Figure 12:
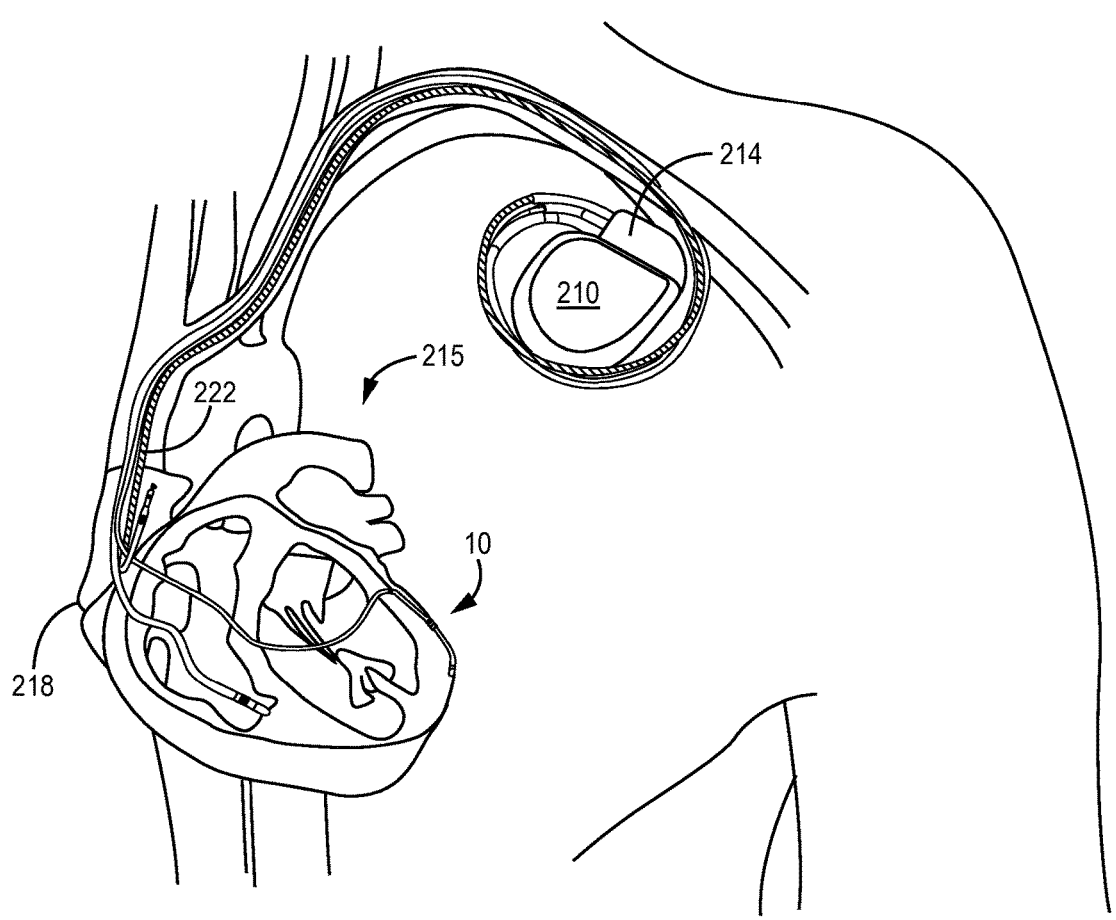
FIG. 12 is a schematic diagram of the exemplary IMD of FIG. 11 implanted in a patient.

Lead body 150 has a proximal portion, to which a connector module 312 is coupled thereto as shown in FIGS. 11-12. Examples of connector modules may be seen with respect to U.S. Pat. No. 7,601,033 issued Oct. 13, 2009, U.S. Pat. No. 7,654,843 issued Feb. 2, 2010, and assigned to the assignee of the present invention, the disclosure of which are incorporated by reference in their entirety herein. Connector module 312, as illustrated, takes the form of an IS-4 bipolar connector, but any appropriate connector mechanism may be substituted. Connector module 312 electrically couples a proximal end of a lead 10 to various internal electrical components of implantable medical device 210. Lead body 150 is formed by an insulative sheath or liner of a biocompatible polymer surrounding internal metallic conductors. Examples of means to insulate conductors and/or lead construction may be seen with respect to U.S. Pat. No. 8,005,549 issued Aug. 23, 2011, U.S. Pat. No. 7,783,365 issued Aug. 24, 2010, and assigned to the assignee of the present invention, the disclosure of which are incorporated by reference in their entirety herein.

The conductors extend from electrodes 104a-d to connector 312, coupling the electrodes 104a-d to contacts in-line bipolar connector 312 in a conventional fashion. Anchoring sleeve 180 is used in a conventional fashion to stabilize the lead and seal the venous insertion site.

Figure 6A:
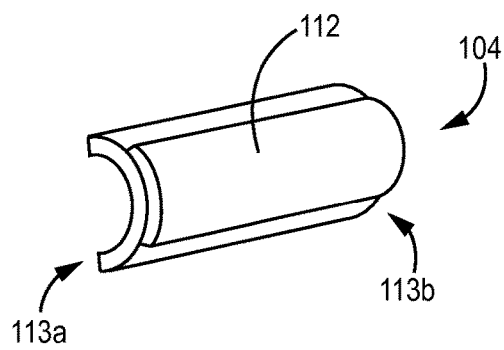
FIG. 6A is a schematic view of a top surface of an electrode that is configured to protrude away from the outer circumference of the lead body.
Figure 6B:
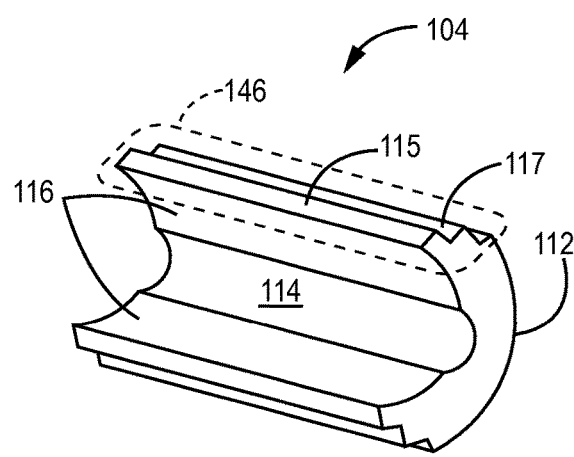
FIG. 6B is a plan view of the inner surfaces of the electrode depicted in FIG. 6A.
Figure 6C:
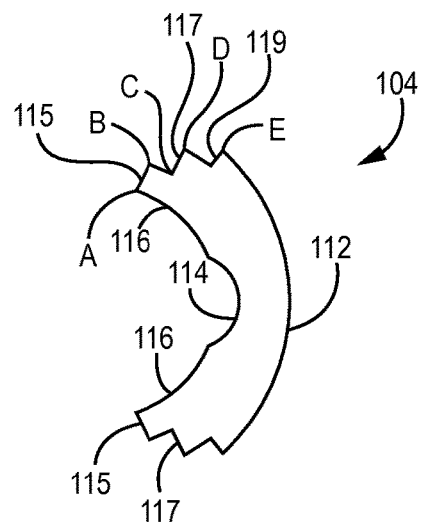
FIG. 6C is a schematic view of inner surfaces of the electrode depicted in FIG. 6A.

Electrodes 104*a-d* can take the form of ring and barrel shaped electrodes, respectively, provided with ring-shaped or other shaped steroid eluting MCRD's as described in U.S. Pat. No. 8,825,180 by Bauer, et al., incorporated herein by reference in its entirety. Other known electrode designs may of course be substituted. Each electrode is configured to have a smaller electrically active surface area to attain higher impedance compared to conventional electrodes. For example, the electrically active surface area of electrode 104*a-d* shown in FIG. 6 is about 2.3 square millimeters (mm$^2$) out of a total surface area of 2.9 mm$^2$, which is equal or slightly less than half the surface area of conventional ring electrodes of 5.8 mm$^2$. In one or more embodiments, the electrodes 104*a-d* are either machined or made from a mold to form the exemplary shapes shown in FIGS. 6A-6C.

Referring to FIG. 2B, a non-conductive portion 110 is positioned over or coupled to the outer surface of each ring electrode 104*a-d* in order to prevent electrical stimuli emanating from a portion of each electrode. To limit the range of electrical stimuli from the active portion of the electrode 104*a-d*, insulated portion 110 extends along the outer circumference and the longitudinal length of the electrode 104. For example, insulated portion 110 can extend about the length and width of the electrode along one side of the lead. Insulated portion 110 partially surrounds electrode 104*a-d* in the range of about 120 degrees to about 360 degrees. Exemplary thickness of polymer (e.g. urethane, urethane adhesive etc.) over a portion of the outer circumference of the electrode can range from about 0.0001 inches to about 0.003 inches. Since the insulated portion 110 covers part of electrode 104*a-d*, the electrical stimuli emanates solely from the electrode's bare or uninsulated portion (also referred to as the active portion) shown in FIG. 2B. Referring to FIG. 2D, electrical stimuli can be delivered in the range of up to 100 degrees, referred to as y, and along the length and/or width of the active portion of electrode 104*a-d*. Electrical stimuli does not conduct through non-conductive portion 110 shown in FIG. 2C which prevents electrical stimuli being delivered of up to 260 degrees around the electrode 104. In another embodiment, the electrical stimuli can extend around the active portion (i.e. bare or uninsulated portion) of the electrode in the range of 0 degrees up to 140 degrees. In this latter example, electrical stimuli does not conduct through non-conductive portion 110 (i.e. up to 220 degrees). In yet another embodiment, the electrical stimuli can extend around the active portion of the electrode in the range of 100 degrees to about 140 degrees.

In one or more embodiments, a non-conductive mechanical mechanism, such as a housing, can be used for securing and insulating the electrode 104*a-d* to the lead body. One exemplary non-conductive electrode housing 160 is shown in FIGS. 7A-7G comprising a polymer exhibiting a durometer ranging from about 30 D to about 50 D or 55 D. The electrode housing 160 is substantially cylindrical in shape with a first end 168 configured to mate with the electrode 104*a-d* and a second end 162 of base portion 164 seated longitudinally in the lead body, as shown in FIG. 2.

Figure 7A:
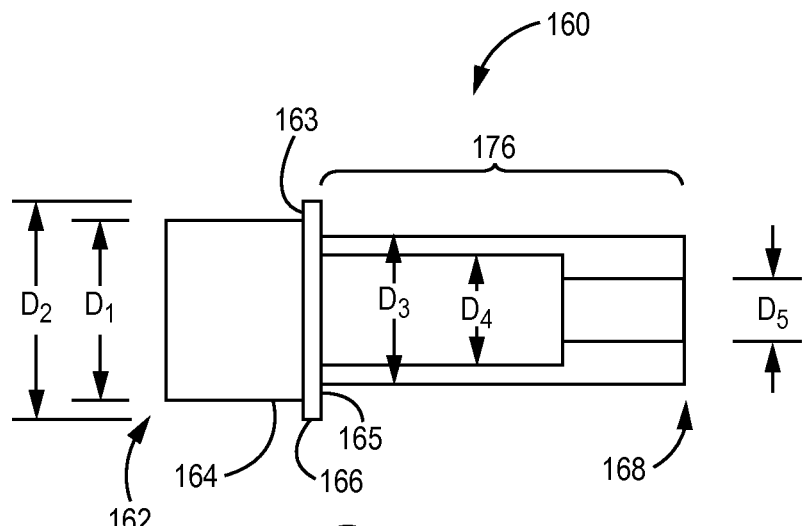
FIG. 7A is a cross-sectional view of a non-conductive electrode housing along a longitudinal axis.
Figure 7B:
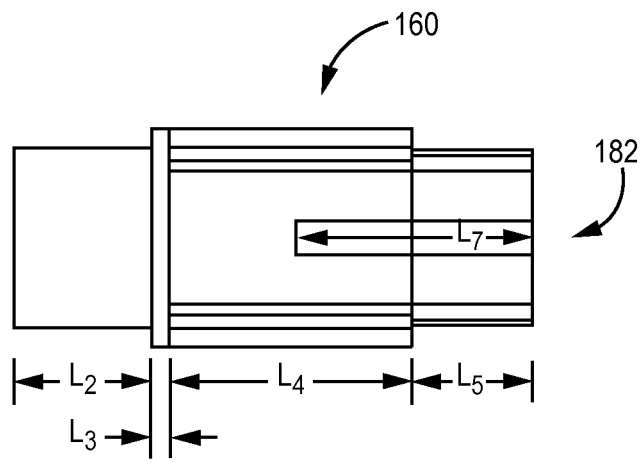
FIG. 7B is a cross-sectional view of the non-conductive electrode housing along a longitudinal axis shown in FIG. 7A but rotated 90 degrees away from the position shown in FIG. 7B.
Figure 7C:
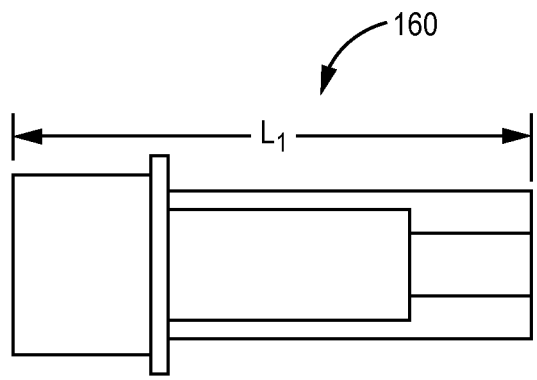
FIG. 7C is the same cross-sectional view as FIG. 7A of the non-conductive electrode housing that shows the total length of the electrode housing.

Referring to FIGS. 7A-7C, housing 160 extends a total length of L1, which comprises lengths L2, L3, L4 and L5. The base portion 164 includes inner and outer diameters D1, D2 respectively and extends a length L2 (also referred to as 164). D1 is about 0.052 inches and D2 is about 0.062 inches. The length L2 of base 162 is about 0.040 inches.

Figure 7D:
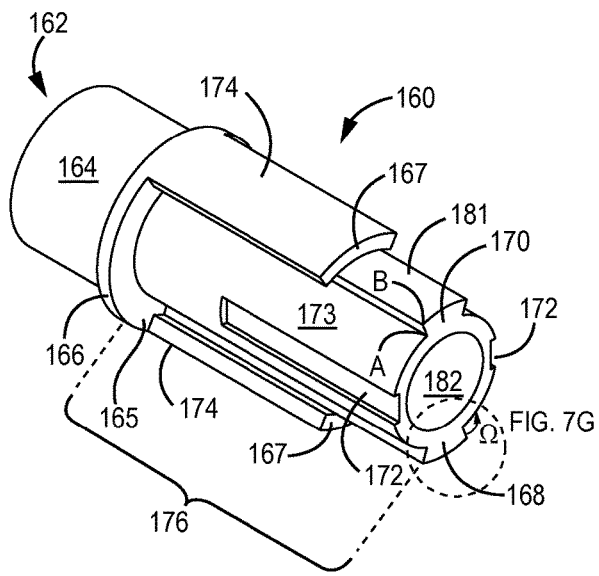
FIG. 7D is a schematic view of the non-conductive electrode housing shown in FIGS. 7A-7C.
Figure 7G:
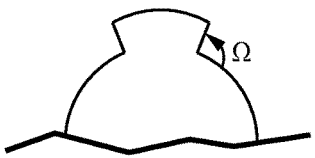
FIG. 7G depicts angle Ω between housing ends of the housing shown in FIG. D.

Referring to FIG. 7D, the electrode receptacle portion 176 of housing 160 has a length comprising lengths L3 (also referred to as 166), L4, and L5, which is about 0.110 inches. The electrode receptacle portion 176 includes inner and outer diameters D3, D4, respectively and D5 as shown in FIG. 7. D3 is about 0.42 inches while D4 is about 0.031 inches. Bore 182 has a diameter D5, configured to receive the conductor, which is about 0.018 inches and extends about L7 or about 0.070 inches.

The outer circumference or surface 173 of housing 160 includes one or more one or more protrusions 170, flange or rails configured to engage with a guide aid 146 of a raised electrode 104 shown in FIGS. 6B-6C. Housing 160 is formed by injection molding or any other suitable thermoforming process. A polymer such as polyurethane can be used in a mold formed to produce housing 160 or introduced over the electrode(s).

Figure 7E:
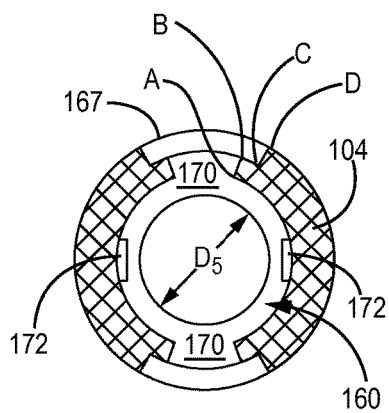
FIG. 7E is a cross-sectional view of an electrode secured within the non-conductive electrode housing shown in FIGS. 7A-D.
Figure 7F:
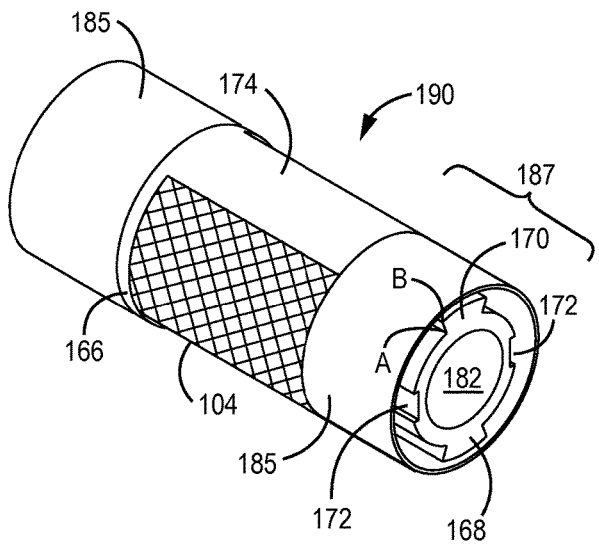
FIG. 7F is a schematic view of an electrode assembly in which the electrode is flush with the housing.

Guide aid 146 can be consecutive L-shapes (or substantially L-shaped) protrusions or a set of steps that extend longitudinally from a first end 113*a* to a second end 113*b*. Referring to FIG. 7E, lip 115 (also referred to as a protrusion) engages with corresponding protrusion 170 of housing 160 such that electrode ends 115*a* and 115B correspondingly engage with housing ends 170A and 170B shown in FIGS. 7D and 7F. Referring to FIG. 7F, angle Ω in the range of 90 degrees exists between housing ends 170A and 170B thereby assisting in forming a more secure engagement between housing 160 and electrode 104 since protrusion partially extends over lip end 115*a*. Simultaneous to electrode lip 115 engaging housing protrusion 170, electrode protrusion 117 at ends 117C and 117D correspondingly engage with housing protrusion 174 at ends 167C and 167D. Referring to FIG. 6, the inner surface 114 of the electrode 104 is configured to mate with an elongated conductor extending from the lead body while electrode inner surface 116 mates with the outer surface 173 of housing 160.

Raised electrode portion 112, shown in FIGS. 6A-6C, does not have a direct engagement with housing 160. Instead, the raised electrode portion 112 protrudes away electrode protrusion 117 and extends beyond lead body to allow the raised electrode portion 112 to more easily contact tissue. Raised electrode portion 112 includes surface 119 shown in FIG. 6C.

Electrode 104 is slid proximally along the inner protrusions or rails 170 of housing 160 until a distal surface of the electrode 104 contacts a distal inner surface 163 of housing 160. Electrode 104 is optionally retained in this position by means of engaging a short rail (not shown), extending from the inner surface of housing 160, with a groove (not shown) at the distal end of the electrode 160. After the electrode is fully engaged with housing 160, the electrode assembly 190 is connected to the conductor. The conductor is placed in groove 172 and can be welded or crimped to the electrode using conventional means. The tubing or liner 185 can then be introduced over base 164 and end 187 shown in FIG. 7F. The tubing or liner 185 of the lead body 15 surrounds the outer circumference of base 164 from second end 162 and extends to surface 165. Additionally, the tubing or liner 185 surrounds or is introduced over surfaces 173 and 181 and extends from surface 167 to first end 168.

Figure 9:
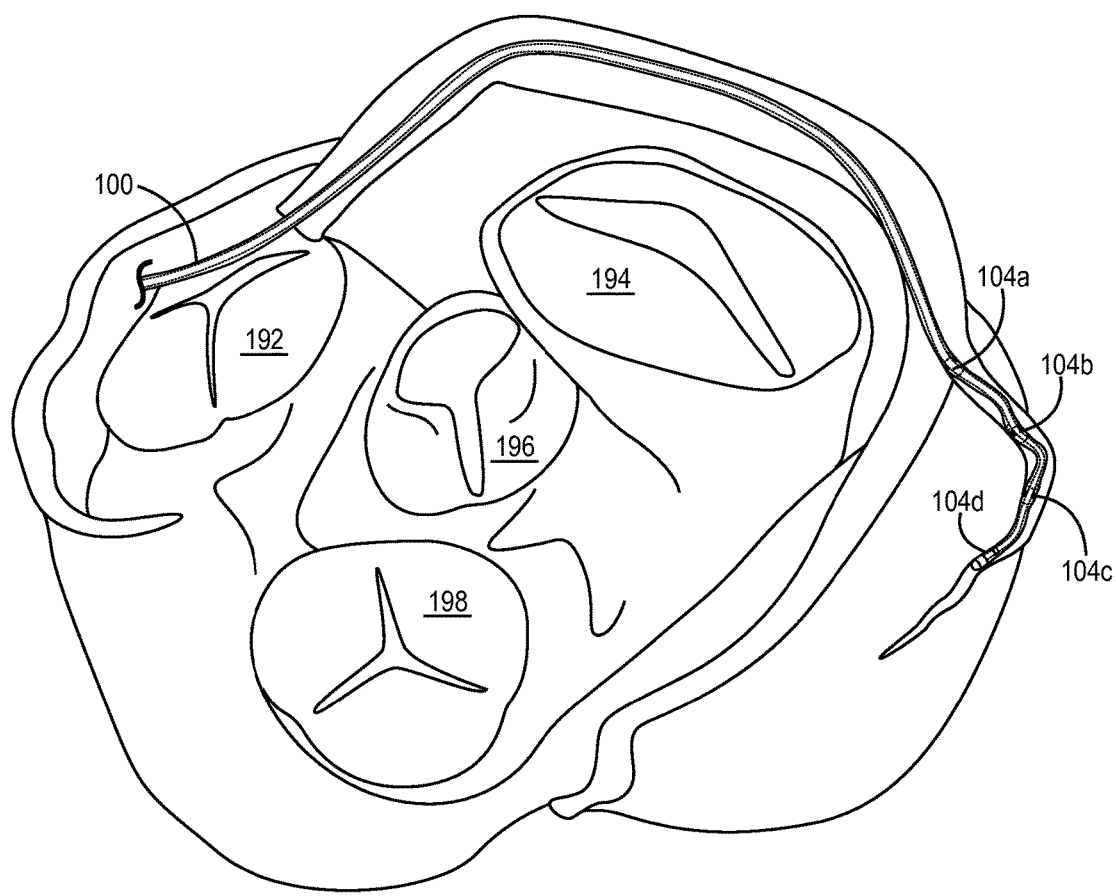
FIG. 9 is a schematic view of a top portion of a human heart and of the lead of FIG. 1 as implanted.

Numerous non-conductive materials can be used to form electrode housing 160. For example, in one or more embodiments, a polymer (e.g. urethane, urethane adhesive etc.) exhibiting a durometer ranging from about 30 D to about 35 D can be used to form housing 160. In one or more other embodiments, a polymer (e.g. urethane, urethane adhesive etc.) exhibiting a durometer ranging from about 35 D to about 40 D can be used to form housing 160. In one or more other embodiments, a polymer (e.g. urethane, urethane adhesive etc.) exhibiting a durometer ranging from about 40 D to about 45 D can be used to form housing 160. In one or more other embodiments, a polymer (e.g. urethane, urethane adhesive etc.) exhibiting a durometer ranging from about 45 D to about 50 D can be used to form housing 160. In one or more other embodiments, a polymer (e.g. urethane, urethane adhesive etc.) exhibiting a durometer ranging from about 50 D to about 55 D can be used to form housing 160. Additionally, any combination of polymers as listed above can be used to form housing 160. Numerous methods exist for placing lead 10 near and/or into excitable tissue (e.g. cardiac tissue such as myocardial tissue). One such method 200, depicted in FIG. 5, describes lead placement corresponding to the positioning of the lead 10 as illustrated in FIGS. 1-4. A lead delivery device (e.g. stylet, guide wire, hybrid guidewire/stylet etc.), such as the ATTAIN HYBRID®, is inserted into an aperture at a proximal end of lead 10. Lead 10 is then inserted directly through an integrated valve of a guide catheter such as Medtronic's ATTAIN CATHETER®. Lead 10 is introduced into the vascular system (step 202, FIG. 5) by any conventional technique. It is desirable, however, that the physician insert lead 10 such that the active portion of electrodes 104*a-d* face in a downward direction of the guide catheter when looking at the top view of the heart as shown in FIG. 9. The lead 10 is then moved into the vasculature (e.g. coronary venous system etc.) to a desired location, for example by advancing the lead body 150 by means of the guide catheter. The coronary venous system includes the coronary sinus vein, great cardiac vein, middle cardiac vein, left posterior ventricular vein, and/or any other applicable cardiac veins. Lead 10 passes through the coronary sinus and into a cardiac vein extending therefrom, while substantially maintaining lead body 150 shape.

Figure 8:
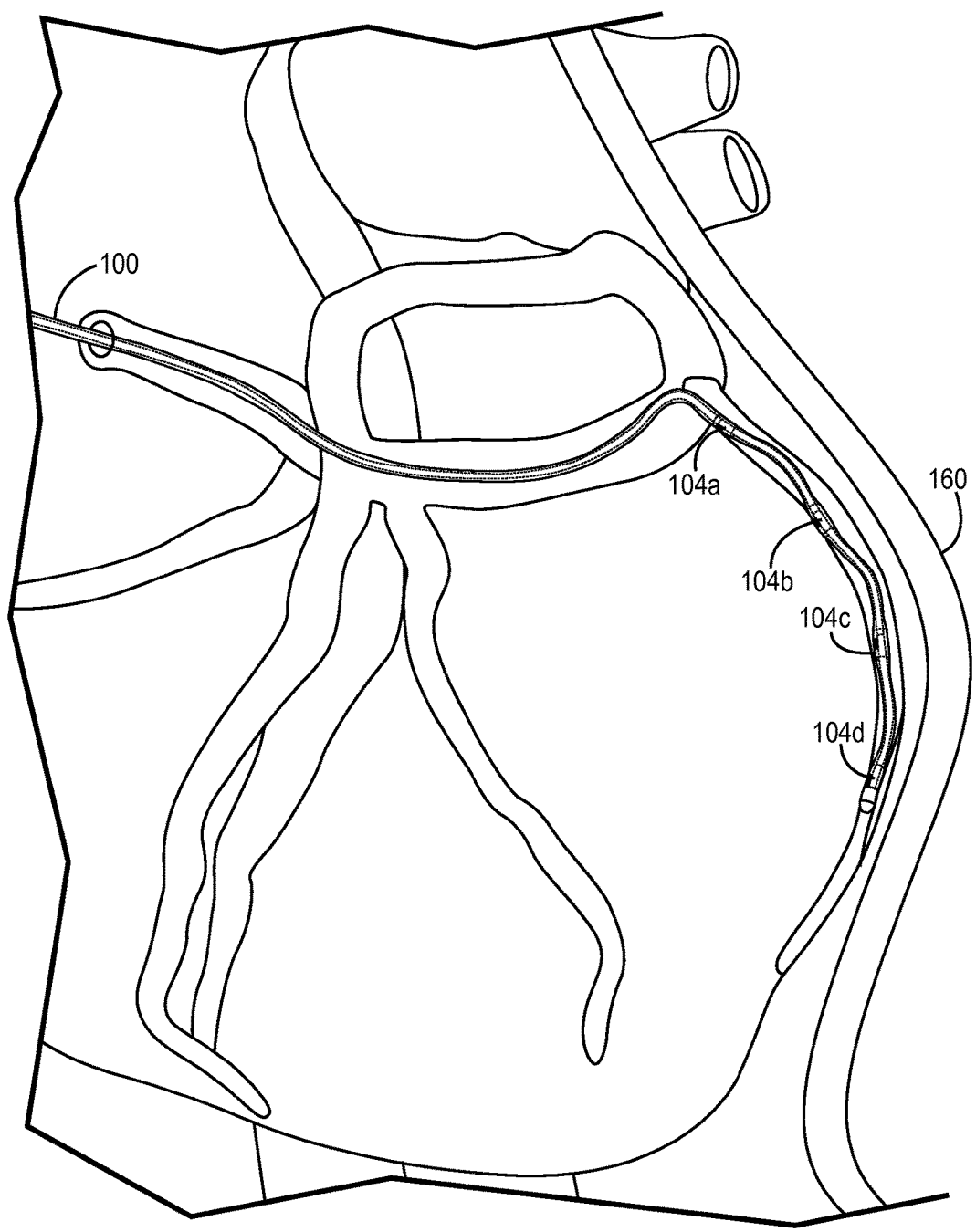
FIG. 8 is a schematic view of a human heart and of the lead depicted in FIG. 1 through the coronary sinus and lateral vein as implanted.

The lead 10 is then advanced further into the coronary venous system (Step 204, FIG. 10 and FIGS. 8-9) around tricuspid valve 192, the mitral valve 194, the aortic valve 196 and the pulmonary valve 198 and generally travels in a downward path of the coronary vein along the naturally curved shape of the heart. This may be accomplished by passing the lead 10 through a guide catheter, or by advancing the lead 10 over a guidewire or by means of a stylet inserted into the lead 10. A hybrid guidewire/stylet may also be used to place a lead 100 near or adjacent myocardial tissue. Any conventional mechanism for placing the lead 10 into and within the coronary venous system may be employed.

While in the coronary venous system, lead 10 cannot easily flip or rotate. Even if the lead 10 is flipped, twisted or rotated while moving through the guide catheter such that the insulated portion of the electrodes face the myocardium, the mechanical structure (e.g. angle of the curve(s) in distal end 120) and/or the stiffness of curved distal end 120 in conjunction with the curved shaped heart causes a rotational force to rotate back to the configuration in which the electrically active portion of lead 10 faces and hugs myocardial tissue, as shown in FIG. 3.

Figure 10:
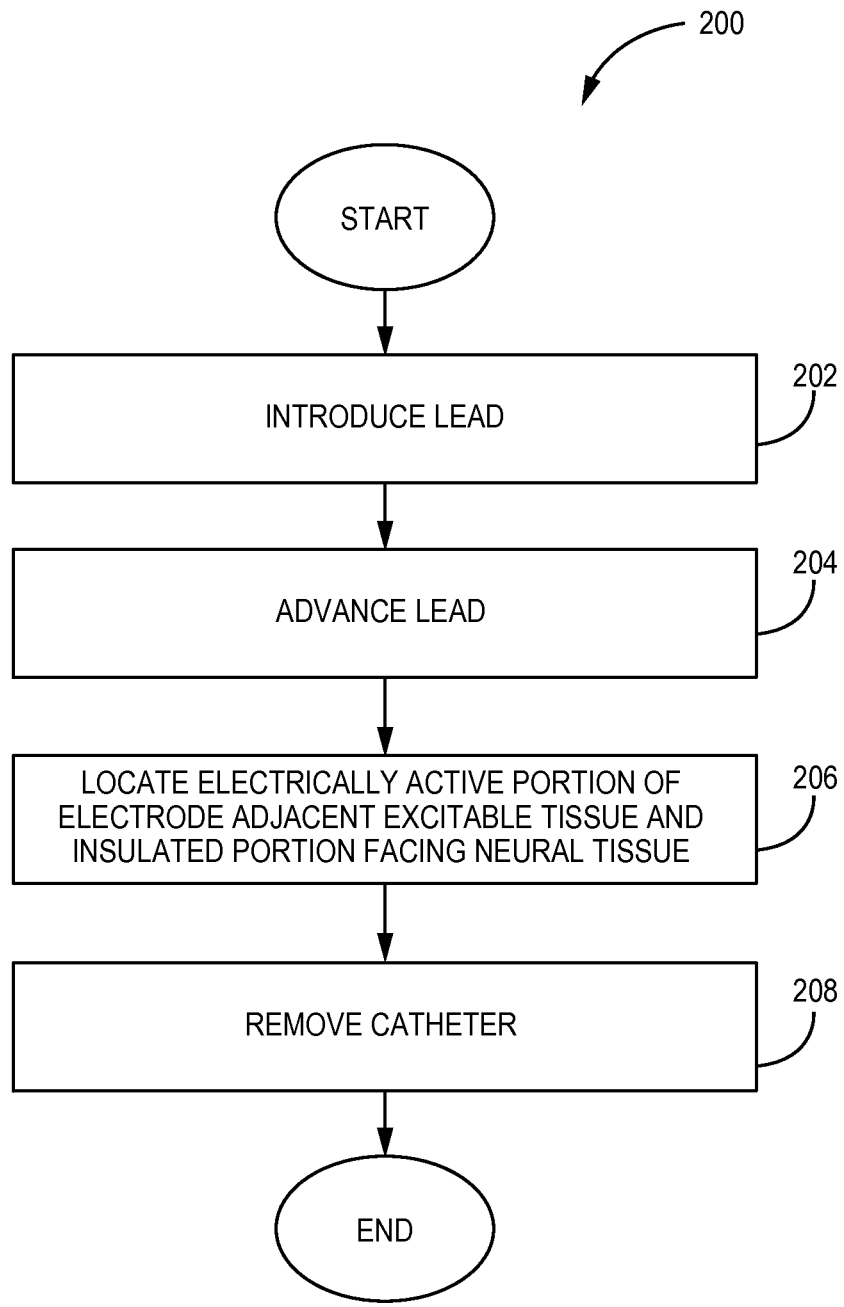
FIG. 10 is a flow chart illustrating the steps of implantation of a lead according to the present disclosure.

Lead 10 is located at an appropriate location, as determined by the physician (Step 206, FIG. 10). Thereafter, the lead body 150 may be moved (i.e. advanced and/or retracted) through the guide catheter until the electrodes 104*a-d* are located in a desirable position (Step 206, FIG. 10). Determination of the position for electrode location may be accomplished by any conventional method, such as pacing threshold testing and/or measurement of R-wave amplitudes. The guide catheter analyzer cable interface 32 is useful to perform this function. Alternatively or additionally, appropriate electrode locations may also be determined based upon determinations of hemodynamic characteristics of the heart as associated with stimulation of heart tissue at various electrode locations.

The shape of lead 10 and/or the weight of the polymer (e.g. housing 160 etc.) over the outer circumference of each electrode causes the lead 10 to exit the guide catheter such that the electrically active portion of the electrodes, disposed along a same longitudinal plane, are exposed to the intended preferred excitable tissue (e.g. myocardial tissue). In contrast, the insulated outer circumference of the electrodes face neural tissue (e.g. the phrenic nerve) towards pericardial surface.

Once the electrodes 104 are placed at the desired location, (Step 208, FIG. 10) any equipment not intended for long term implant, e.g. guide catheter, stylet, guidewire, etc. can be removed. Repositioning of the electrodes after implant may also be possible.

By using a lead 10 with a set of electrodes 104*a-d* that are configured to move through the coronary sinus in a manner such that the electrically active portion of the set of electrodes 104*a-d* finds its way to the myocardial tissue, pacing toward the myocardium becomes more efficient. Increased efficiency of pacing allows each electrode decrease or have a smaller surface area electrode for higher impedance. For example, a large surface area current electrode can be 5.8 mm$^2$ surface electrodes while the present disclosure employs a 2.3 mm$^2$ to 2.9 mm$^2$, which is slightly less or equal than half the surface area of conventional electrodes. The smaller surface area of the electrode raises the impedance which reduces the amount of current drain. The smaller electrode surface area located on lead 10, directed 104*a-d* towards the myocardium, is believed to assist in achieving good thresholds (i.e. voltage required to capture the heart) and higher impedance.

FIGS. 11-12 depict conceptual diagrams illustrating an exemplary therapy system 210 that may be used to deliver pacing therapy to a patient 214 using S-shaped lead 10. The therapy system 210 may include an implantable medical device 210 (IMD), which may be coupled to leads 10, 218, 222. The IMD 210 may be, e.g., an implantable pacemaker, cardioverter, and/or defibrillator, that provides electrical signals to the heart 215 of the patient 214 via electrodes coupled to one or more of the leads 10, 218, 222.

The leads 10, 218, 222 extend into the heart 215 of the patient 214 to sense electrical activity of the heart 215 and/or to deliver electrical stimulation to the heart 215. In the example shown in FIG. 11, the right ventricular (RV) lead 218 extends through one or more veins (not shown), the superior vena cava (not shown), and the right atrium 226, and into the right ventricle 228. The left ventricular (LV) coronary sinus lead 10 extends through one or more veins, the vena cava, the right atrium 226, and into the coronary sinus to a region adjacent to the free wall of the left ventricle 232 of the heart 215. The right atrial (RA) lead 222 extends through one or more veins and the vena cava, and into the right atrium of the heart 215.

The IMD 210 may sense, among other things, electrical signals attendant to the depolarization and repolarization of the heart 215 via electrodes coupled to at least one of the leads 10, 218, 222. The IMD 210 may be configured to determine or identify effective electrodes located on the leads 10, 218, 222 using the exemplary methods and processes described herein. In some examples, the IMD 210 provides pacing therapy (e.g., pacing pulses) to the heart 215 based on the electrical signals sensed within the heart 215. The IMD 210 may be operable to adjust one or more parameters associated with the pacing therapy such as, e.g., AV delay and other various timings, pulse wide, amplitude, voltage, burst length, etc. Further, the IMD 210 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 210 may also provide defibrillation therapy and/or cardioversion therapy via electrodes located on at least one of the leads 10, 218, 222. Further, the IMD 210 may detect arrhythmia of the heart 215, such as fibrillation of the ventricles 228, 232, and deliver defibrillation therapy to the heart 215 in the form of electrical pulses. In some examples, IMD 210 may be programmed to deliver a progression of therapies, e.g., pulses with increasing energy levels, until a fibrillation of heart 215 is stopped.

Figure 13:
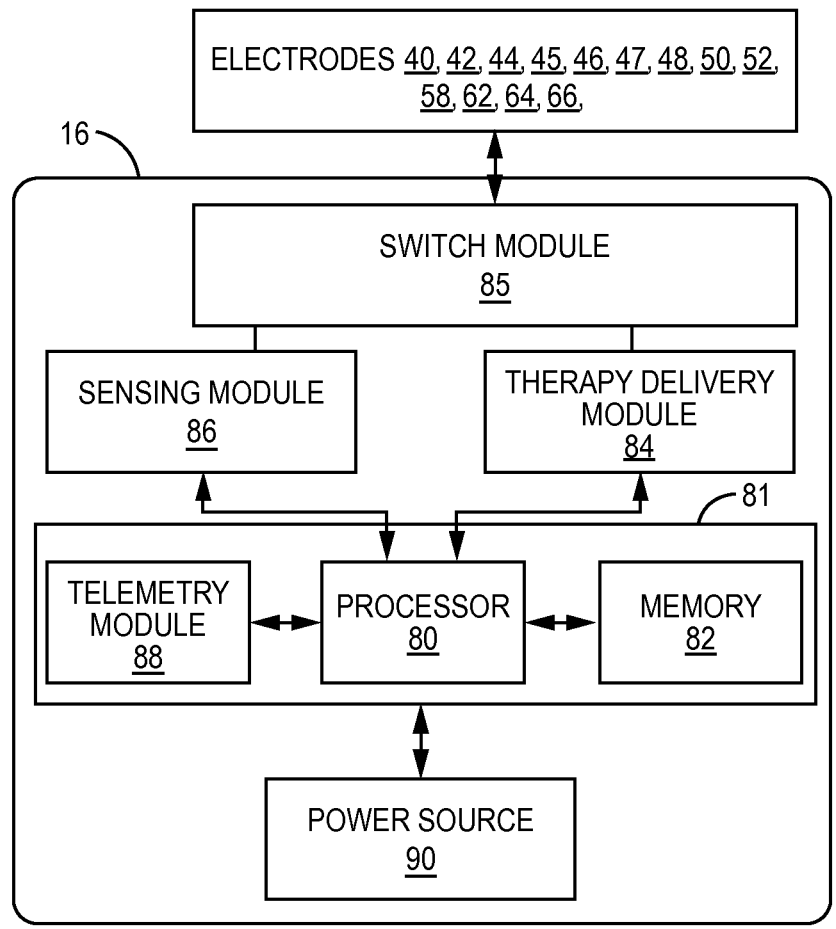
FIG. 13 is a block diagram of an exemplary IMD, e.g., the IMD of FIGS. 1-2.

FIG. 13 is a functional block diagram of one exemplary configuration of the IMD 216. As shown, the IMD 216 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 216 and/or the control module 81 to perform various functions attributed to the IMD 216 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may be used to determine the effectiveness of the electrodes 40, 42, 44, 45, 46, 47, 48, 50, 58, 62, 64, 66 using the exemplary methods and/or processes described herein according to a selected one or more programs, which may be stored in the memory 82. Further, the control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, pacing pulses with the amplitudes, pulse widths, frequency, or electrode polarities, etc., which may be specified by one or more selected therapy programs (e.g., AV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 218, 10, 222, or, in the case of housing electrode 58, via an electrical conductor disposed within housing 60 of IMD 216. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 218, 10, and 222, respectively, and/or helical tip electrodes 42 and 50 of leads 218 and 222. Further, for example, therapy delivery module 84 may deliver defibrillation shocks to heart 15 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 216 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may be also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 216 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 14:
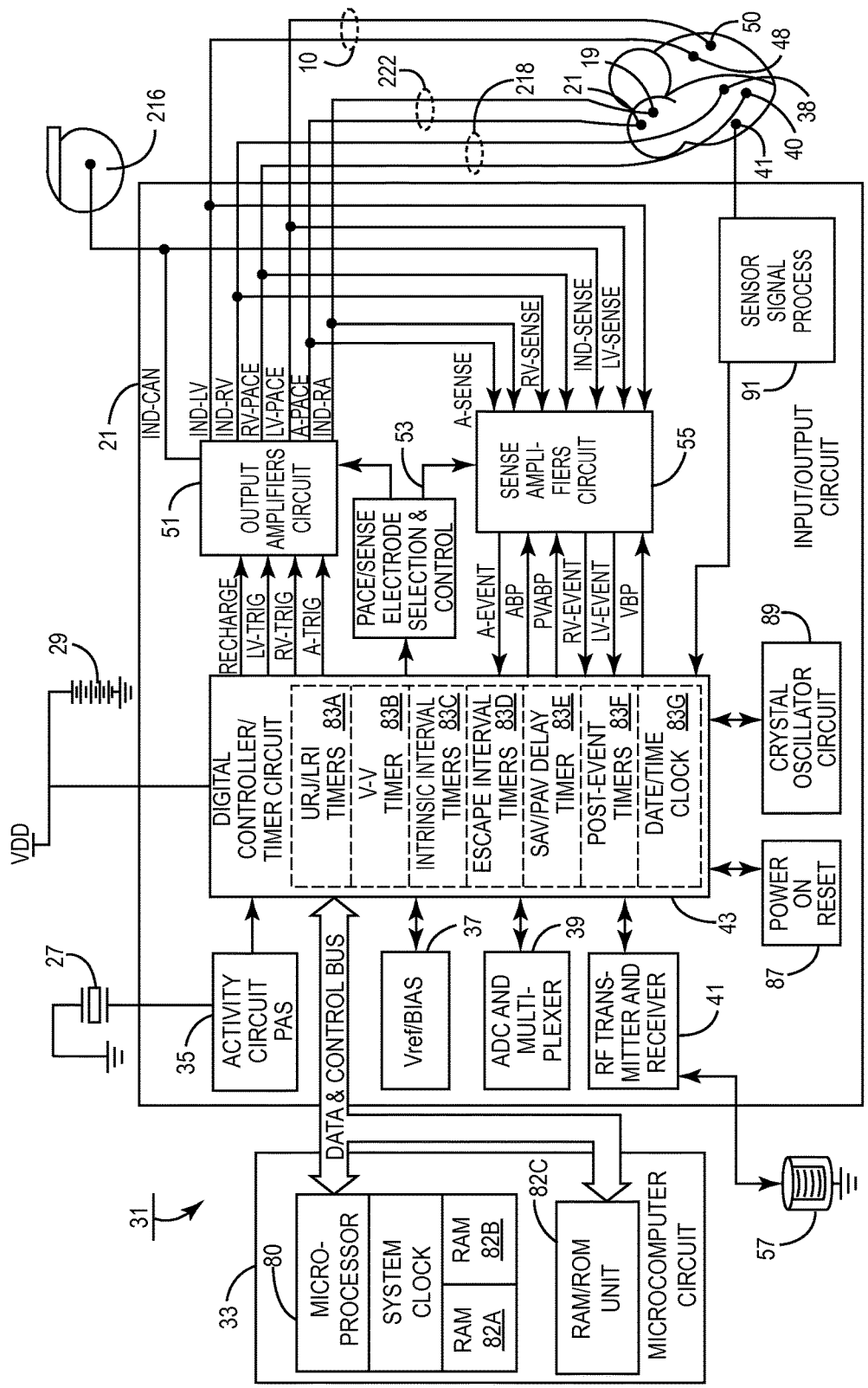
FIG. 14 is another block diagram of an exemplary IMD (e.g., an implantable pulse generator) circuitry and associated leads employed in the system of FIGS. 1-2 for providing three sensing channels and corresponding pacing channels.

FIG. 14 is another embodiment of a functional block diagram for IMD 216. FIG. 14 depicts bipolar RA lead 222, bipolar RV lead 218, and bipolar LV CS lead 10 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 87 and crystal oscillator circuit 89 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which are incorporated herein by reference in their entireties. Similarly, the exemplary systems, apparatus, and methods described herein may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and marker channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as determined using known methods) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F time out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 216, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Figure 15:
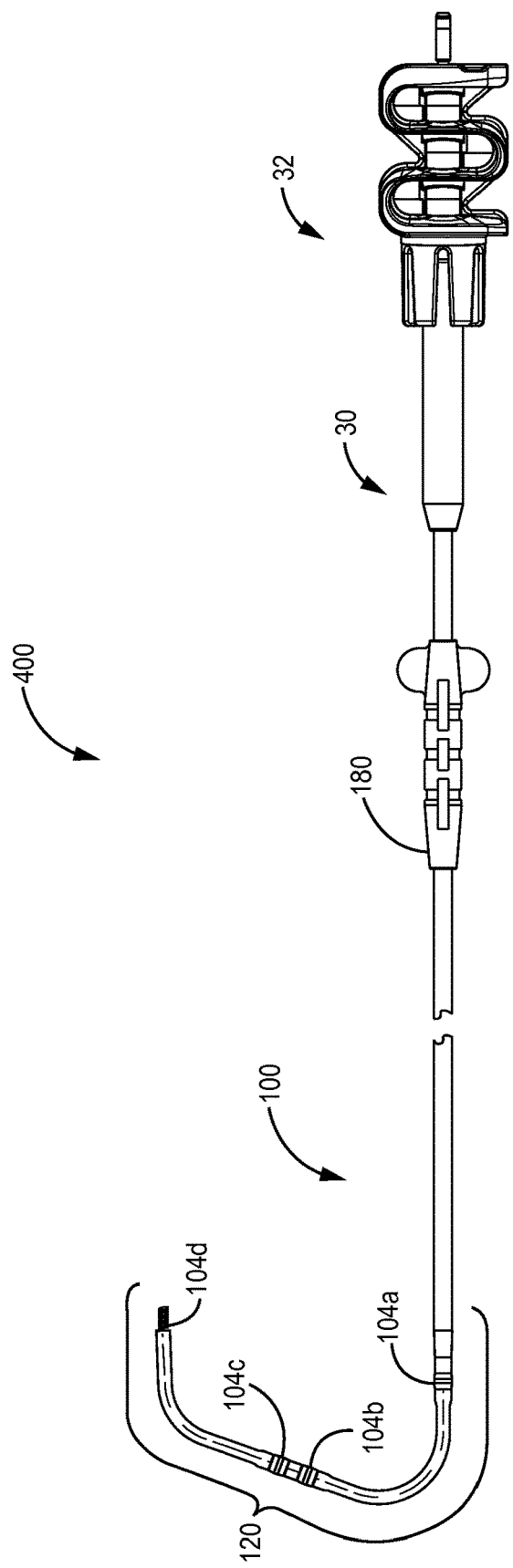
FIG. 15 is a plan view generally illustrating, a J-shaped lead, according to a fourth embodiment.

Many alternatives leads can employ the teaching disclosed herein. For example, alternative medical electrical leads can include active or passive fixation mechanisms (e.g. helix, tines, adhesive etc.). For example, FIG. 15 depicts a substantially J-shaped lead 400. J-shaped lead 400 can include a set of electrodes 104*a*-*d* that are masked along a first longitudinal plane and the electrically active portion of electrodes along a second longitudinal plane that is diametrically opposed to the first longitudinal plane.

Additionally, while FIGS. 2-3 illustrate the electrodes 104*a*-*d* as advancing through the coronary sinus, it should be understood that other locations in the heart's venous system may also be accessed using this lead. Electrode placement may alternatively be optimized for atrial stimulation and/or sensing. Alternatively, the lead may be useful in other vascular or non-vascular location within the body wherein the distance between a suitable fixation location and a desired electrode location may be variable.

Numerous alternatives exist to the embodiments disclosed herein. While non-conductive portion 110 can be a mechanical structure engaged with the electrode, non-conductive portion 110 can also be a polymer placed over the electrode. For example, one or more different embodiments can be directed to masking a ring electrode. Each ring electrode 104*a*-*d* can also be configured to be longitudinally aligned along an outer circumference of each electrode 104*a*-*d*.

Any technique can be used to apply the polymer to the outer circumference of the electrode 104*a*-*d*. For example, after lead 10 is manufactured, the polymer can be directly applied to the set of electrodes 104*a*-*d* along the same longitudinal plane while the remaining portion of the electrodes 104*a*-*d* are not covered with polymer and can conduct current to tissue. Alternatively, each electrode 104*a*-*d* can be individually masked and then assembled in a fashion such that each electrically active portion of each electrode 104*a*-*d* is aligned along a same longitudinal plane as another electrically active portion of an electrode while the masked portions of the electrodes 104*a*-*d* align along a different longitudinal plane. Application of the polymer can be performed automatically by a machine operation or manually by an operator using any available technique such as brushing polymer onto the surface of the electrode.

In another alternate embodiment, the one or more grooves are formed on the outer surface of electrode through use of placing molten metal into a mold that is either substantially ring-shaped mold (not shown) or a mold formed to produce the electrode disclosed herein.

The following paragraphs enumerated consecutively from 1 through 24 provide for various aspects of the present disclosure. In one embodiment in a first paragraph (1) the present disclosure provides:

1. An intravenous medical electrical lead, comprising:
an elongated lead body comprising a length between a proximal end and a curved distal end, the lead body defining a longitudinal axis extending between the proximal end and the curved distal end, the lead body having an outer circumference and provided with a set of electrodes circumferentially spaced apart, each electrode having an electrically active portion and an insulated portion at an outer circumference, the lead body further configured to move through a coronary vein while substantially retaining its curved distal end, the curved distal end expanding to its original shape such that the electrically active portion of electrode abuts myocardial tissue while the insulated portion of each electrode face a phrenic nerve of a patient.

2. A lead according to paragraph 1 wherein the electrically active portion at the outer circumference of each electrode are aligned along a same plane of the longitudinal axis and the insulated portion at the outer circumference of each electrode are aligned along a different plane of the longitudinal axis.

3. A lead according to any of paragraphs 1-2 wherein the curved distal end is a single curve end.

4. A lead according to paragraph 3 wherein the curved distal end extends about 3 inches away from a distal tip of the lead.

5. A lead according to any of paragraphs 1-4 wherein the electrode is less than half of a electrode.

6. A lead according to paragraph 5 wherein the electrode protrudes away from an outer circumference of a lead body.

7. A lead according to paragraph 5 wherein the electrode is a electrode.

8. A lead according to any of paragraphs 1-7 wherein the lead distal end is substantially S-shaped.

9. A lead according to any of paragraphs 1-8 wherein the lead distal end is wave-shaped.

10. A lead according to paragraph 5 wherein each masked portion of each electrode weighs more than an unmasked portion of the electrode.

11. A lead according to any of paragraphs 1-10 wherein the lead body being shaped to wrap or hug a curved-shaped heart.

12. A lead according to any of paragraphs 1-11 wherein each electrode includes a convex portion that protrudes away from an outer circumference to the lead body.

13. A lead according to any of paragraphs 1-12 wherein the convex portion is over a base portion of the electrode.

14. A lead according to any of paragraphs 1-13 wherein each electrode is configured to reduce surface area by about 50% or more compared to a surface area of a conventional electrode.

15. A lead according to any of paragraphs 1-14 wherein each electrode is configured to deliver electrical stimulation in a range of about 180° or less compared to 360° employed by conventional electrodes.

16. A lead according to any of paragraphs 1-15 wherein each electrode being configured to radially extend beyond an outer circumference of the lead body.

17. A lead according to any of paragraphs 1-16 wherein the insulated portion partially surrounds each electrode in a range of about 120 degrees to about 360 degrees.

18. A lead according to any of paragraphs 1-17 wherein the active portion of each electrode allows electrical stimuli to extend within a range of about 100 degrees to about 140 degrees.

19. A lead according to any of paragraphs 1-19 wherein the active portion of each electrode allows electrical stimuli to extend up to a maximum of 220 degrees around the electrode.

20. A lead according to any of paragraphs 1-20 wherein the active portion of each electrode allows electrical stimuli to extend up to a maximum of 140 degrees around the electrode.

21. A method of implanting an intravenous medical electrical lead in a patient's body, comprising:

advancing, within in the patient's body, a lead having an elongated lead body defining a longitudinal axis and carrying a set of ring electrodes radially spaced apart, the set of ring electrodes having an electrically active portion at an outer circumference along a same plane of the longitudinal axis while another portion of the set of ring electrodes is insulated at the outer circumference along a different plane of the longitudinal axis; and moving the lead body through a coronary vein while the lead body substantially retaining its curved distal end, the curved distal end exiting a delivery catheter such that the set of ring electrodes exposes a portion of each ring electrode, along a same longitudinal plane, to excitable tissue while another portion of each electrode, covered with insulation, face neural tissue body.

22. A method according to paragraph 21 wherein locating the electrode comprises moving the lead body longitudinally relative to the delivery catheter.

23. A method according to paragraph 21 wherein the advancing step comprises advancing through the patient's vascular system.

24. A method according to paragraph 21 wherein the desired location of the electrode is with the patient's coronary venous system.

25. A method according to any of paragraphs 21-24 wherein the electrically active portion at the outer circumference of each electrode are aligned along a same plane of the longitudinal axis and the insulated portion at the outer circumference of each electrode are aligned along a different plane of the longitudinal axis.

26. A method according to any of paragraphs 21-25 wherein the curved distal end is one of a single curve end.

27. A method according to any of paragraphs 22-26 wherein each ring electrode has half or more of its surface area insulated at the outer circumference of each ring electrode.

28. A method according to paragraph 22 wherein the lead distal end is substantially S-shaped.

29. A method according to paragraph 22 wherein the lead distal end is wave-shaped.

30. A method according to any of paragraphs 21-29 wherein each insulated portion of each electrode weighs more than a bare portion of the electrode.

31. A method according to any of paragraphs 21-30 wherein the insulated portion partially surrounds each electrode in a range of about 120 degrees to about 360 degrees.

32. A method according to any of paragraphs 21-30 wherein the active portion of each electrode allows electrical stimuli to extend within a range of about 100 degrees to about 140 degrees.

33. A method according to any of paragraphs 21-30 wherein the active portion of each electrode allows electrical stimuli to extend up to a maximum of 220 degrees around the electrode.

34. A method according to any of paragraphs 21-30 wherein the active portion of each electrode allows electrical stimuli to extend up to a maximum of 140 degrees around the electrode.

35. A system of delivering therapy through an intravenous medical electrical lead in a patient's body, comprising:

means for advancing, within in the patient's body, a lead having an elongated lead body defining a longitudinal axis and carrying a set of ring electrodes radially spaced apart, the set of ring electrodes having an electrically active portion at an outer circumference along a same plane of the longitudinal axis while another portion of the set of ring electrodes is insulated at the outer circumference along a different plane of the longitudinal axis; and means for moving the lead body through a coronary vein while the lead body substantially retaining its curved distal end, the curved distal end exiting a delivery catheter such that the set of ring electrodes exposes a portion of each ring electrode, along a same longitudinal plane, to excitable tissue while another portion of each electrode, covered with insulation, face neural tissue body.

In the foregoing detailed description, the invention has been described with reference to specific embodiments. However, it may be appreciated that various modifications and changes can be made without departing from the scope of the invention as set forth in the appended claims.

The invention claimed is:

1. An intravenous medical electrical lead, comprising:

an elongated lead body comprising a length between a proximal end and a curved distal end, the lead body defining a longitudinal axis extending between the proximal end and the curved distal end, the lead body having an outer circumference and provided with a set of electrodes circumferentially spaced apart, each electrode having an electrically active portion and an insulated portion at an outer circumference, the lead body further configured to move through a coronary vein while substantially retaining its curved distal end, the curved distal end expanding to its original shape such that the electrically active portion of each electrode abuts myocardial tissue while the insulated portion of each electrode faces a phrenic nerve of a patient, wherein the lead has a mechanical structure such that if the insulated portions face the myocardial tissue, the mechanical structure provides a rotational force to rotate the electrically active portions to face the myocardial tissue.

2. A lead according to claim 1 wherein the curved distal end is a single curve end.

3. A lead according to claim 2 wherein the curved distal end extends about 3 inches away from a distal tip of the lead.

4. A lead according to claim 1 wherein the electrode protrudes away from an outer circumference of a lead body.

5. A lead according to claim 1 wherein the lead distal end is substantially S-shaped.

6. A lead according to claim 1 wherein the lead distal end is wave-shaped.

7. A lead according to claim 1 wherein the lead body being shaped to wrap or hug a curved-shaped heart.

8. A lead according to claim 1 wherein each electrode includes a convex portion that protrudes away from an outer circumference to the lead body.

9. A lead according to claim 1 wherein the convex portion is over a base portion of the electrode.

10. A lead according to claim 1 wherein each electrode is configured to deliver electrical stimulation in a range of about 180° or less compared to 360° employed by conventional electrodes.

11. A lead according to claim 1 wherein each electrode being configured to radially extending beyond an outer circumference of the lead body.

12. A lead according to claim 1 wherein the insulated portion partially surrounds each electrode in a range of about 120 degrees to about 360 degrees.

13. A lead according to claim 1 wherein the active portion of each electrode allows electrical stimuli to extend within a range of about 100 degrees to about 140 degrees.

14. A lead according to claim 1 wherein the active portion of each electrode allows electrical stimuli to extend up to a maximum of 220 degrees around the electrode.

15. A lead according to claim 1 wherein the active portion of each electrode allows electrical stimuli to extend up to a maximum of 140 degrees around the electrode.

16. An intravenous medical electrical lead, comprising:

an elongated lead body comprising a length between a proximal end and a curved distal end, the lead body defining a longitudinal axis extending between the proximal end and the curved distal end, the lead body having an outer circumference and provided with a set of electrodes circumferentially spaced apart, each electrode having an electrically active portion and an insulated portion at an outer circumference, the lead body further configured to move through a coronary vein while substantially retaining its curved distal end, the curved distal end expanding to its original shape such that the electrically active portion of electrode abuts myocardial tissue while the insulated portion of each electrode face a phrenic nerve of a patient; and wherein the electrically active portion at the outer circumference of each electrode are aligned along a same plane of the longitudinal axis and the insulated portion at the outer circumference of each electrode are aligned along a different plane of the longitudinal axis.

* * * * *